United States Patent [19]
O'Lenick, Jr.

[11] Patent Number: 5,780,643
[45] Date of Patent: Jul. 14, 1998

[54] MEADOWFOAM IMIDAZOLINES

[75] Inventor: Anthony J. O'Lenick, Jr., Lilburn, Ga.

[73] Assignee: Fan Tech Ltd., Chicago, Ill.

[21] Appl. No.: 819,555

[22] Filed: Mar. 17, 1997

Related U.S. Application Data

[63] Continuation-in-part of Ser. No. 516,138, Aug. 17, 1995, Pat. No. 5,646,321.

[51] Int. Cl.$^6$ ................. C07D 233/14; B10M 133/44
[52] U.S. Cl. ........................ 548/350.1; 503/283
[58] Field of Search ............ 548/350.1; 508/283

[56] References Cited

U.S. PATENT DOCUMENTS

| | | | |
|---|---|---|---|
| 3,116,252 | 12/1963 | Beretvas | 508/283 X |
| 3,397,146 | 8/1968 | Cupper et al. | 508/283 X |
| 4,189,593 | 2/1980 | Wechsler et al. | 548/350.1 |
| 4,289,486 | 9/1981 | Horodysky et al. | 548/350.1 X |
| 4,536,311 | 8/1985 | Horodysky | 548/350.1 X |
| 5,023,312 | 6/1991 | Erickson et al. | 558/160 |
| 5,530,137 | 6/1996 | Owiti et al. | 548/350.1 |

*Primary Examiner*—Fiona T. Powers

[57] ABSTRACT

The present invention deals with a certain novel imidazoline which are prepared by the reaction of aminoethylethanolamine and meadowfoam fatty, methyl ester or triglyceride. This material is useful as a lubricant additive and as an intermediate to make amphoteric surfactants.

5 Claims, No Drawings

MEADOWFOAM IMIDAZOLINES

RELATED APPLICATIONS

This application is a continuation in part of application Ser. No. 516,138 filed Aug. 17, 1995, now U.S. Pat. No. 5,646,321.

BACKGROUND OF THE INVENTION

1. Field of the Invention

The present invention deals with a novel imidazolines which are prepared by the reaction of an aminoethylethanolamine and meadowfoam fatty, methyl ester or triglyceride. These materials are useful as industrial lubricants where outstanding liquidity, and resistance to oxidation are required. This combination of properties make these compounds excellent candidates as additives to lubricants where the stability and lubrication properties are quite outstanding.

The addition of between 1 and 15% of the novel imidazoline to aqueous cutting fluids and lubricants results in improved lubrication without degradation seen in oleic and other unsaturated imidazolines. The oxidative degradation is usually associated with unsaturation in the molecule.

2. Description of the Art Practices

Imidazolines that are based upon saturated fatty acids are well known. They are described in U.S. Pat. No. 4,458,080 and U.S. Pat. No. 2,155,877, incorporated herein by reference.

Chemically, imidazolines are the reaction product of aminoethyl ethanol amine and a fatty material. Fatty materials are a class of compounds which include fatty carboxylic acids, fatty methyl esters and fatty glycerides (also called oils). The source of the fatty materials may include coconut, peanut, soybean, and rapeseed oils, fractionated and non-fractionated fatty methyl esters and acids of almost any carbon length.

Variation of carbon chain lengths in the fatty source has direct effect upon properties. The best lubricants have between 18 and 20 carbon atoms. Since these materials are solids, the use in many formulations is somewhat limited. The incorporation of oleic acid derivatives or linoleic acid derivatives results in a product that while liquid, has a problem with thermal degradation.

The recent availability of meadowfoam oil, with it's 20 to 22 carbon atoms and the specific location of it's double bonds, and it's reaction to make imidazolines results in the preparation liquid stable imidazoline, acceptable for use in many applications.

Meadowfoam compounds as described herein are selected from the group consisting of meadowfoam oil, meadowfoam fatty acid and meadowfoam methyl ester.

Meadowfoam oil is a triglyceride conforming to the following structure;

R—C(O)—O—CH₂
|
R—C(O)—O—CH
|
R—C(O)—O—CH₂

Meadowfoam fatty acid conforms to the following structure

R—C(O)—OH

Meadowfoam methyl ester conforms to the following structure:

R—C(O)—OCH₃ wherein:
R is derived from meadowfoam and is:
60 14 65% by weight —(CH₂)₃—CH=CH—(CH₂)₁₃—CH₃
12–20% by weight a mixture of

—(CH₂)₃—CH=CH—(CH₂)₁₅—CH₃ and

—(CH₂)₁₁-CH=CH—(CH₂)₇—CH₃ and
15–28% by weight

—(CH₂)₃—CH=CH—(CH₂)₆—CH=CH—(CH₂)₆—CH₃;

None of the prior imidazolines possess the critical meadowfoam moiety. Molecules of the current invention have the meadowfoam alkyl group in the imidazoline.

THE INVENTION

This invention relates to a particular group of imidazolines made by the reaction of meadowfoam oil, meadowfoam methyl ester or meadowfoam fatty acid with aminoethylethanolamine. The terms meadowfoam oil, fatty acid or methyl ester as used herein refer to a specific alkyl distribution of the groups which is are native to a plant Limnathes Alba, commonly called meadowfoam oil. Meadowfoam oil is harvested from a plant and sold commercially by The Fanning Corporation under the tradename "Fancor Meadowfoam".

The unique structure of the oil coupled results in a liquid ester with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the imidazoline having the unique distribution of the meadowfoam on the other result in superior liquidity, lubricity, and outstanding oxidative stability.

The compounds of the current invention are derived from meadowfoam and conform to the following structure;

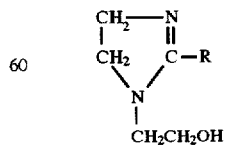

R is derived from meadowfoam and is;
60–65% by weight —(CH₂)₃—CH=CH—(CH₂)₁₃—CH₃
12–20% by weight a mixture of

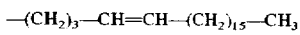

and

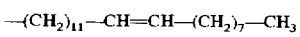

and
15–28% by weight

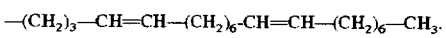

The invention also teaches that an imidazoline can be made the reaction of an aminoethylethanolamine and meadowfoam id as follows:

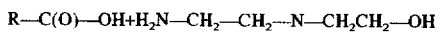

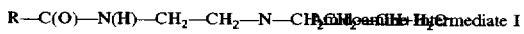 Intermediate I

The amidoamine cyclizes with time and temperature to give the desired product:

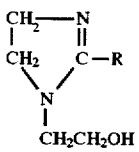

R is derived from meadowfoam.

In a preferred embodiment the reaction is conducted at a temperature of between 180 and 250 C.

EXAMPLES

Example 1

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the triglyceride, glycerine is produced, in the case of the acid water is produced and in the case of the methyl ester methanol is produced.

Aminoethylethanolamine

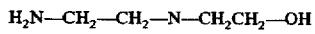

Example 1

Meadowfoam Oil

To 206 grams of aminoethylethanolamine is added then 354.0 grams of the meadowfoam oil. The temperature of the mass is raised to 190–250 C. Glycerine is produced. As the cyclization occurs water is distilled off and reaches theoretical, that is one mole, or 18.0 grams. Any excess amine is stripped off, under vacuum after the water is removed.

Example 2

Meadowfoam Fatty Acid

To 206 grams of aminoethylethanolamine is added then 354.0 grams of the meadowfoam acid. The temperature of the mass is raised to 190–250 C. Water is distilled off. The amount of water distilled off reaches theoretical, that is two moles, or 36.0 grams. Any excess amine is stripped off, under vacuum after the water is removed.

Example 3

Meadowfoam Fatty Methyl Ester

To 206 grams of aminoethylethanolamine is added then 354.0 grams of the meadowfoam methyl ester. The temperature of the mass is raised to 190–250 C. Methanol is distilled off. As the cylcization occurs water distilled off reaches theoretical, that is one mole, or 18.0 grams. Any excess amine is stripped off, under vacuum after the water is removed.

The products are clear liquids which remain liquid to extraordinarily low temperatures. They exhibits outstanding oxidative stability, and lubrication properties when formulated in both aqueous and oil based systems.

Applications Properties

Liquid products which contain unsaturation are subject to an oxidation process referred to as rancidity. The double bond (conjugated or unconjugated) present for the desired liquidity is oxidized to aldehydes and ketones which react to form compounds causing bad color, and odor. In many applications mal odor is an indication of oxidative problems and can itself also be a major problem. The presence of the aldehydic rancidity by-products produce unacceptable odor, and color and have a profound effect upon these properties at very minute concentrations. Studies have shown that the part per billion levels of some aldehydic compounds cause unacceptable properties.

RANCIDITY TESTING

Rancidity was tested using gas chromotography on the head space above the product stored at specific conditions looking for degradation products.

(Addition of 5 grams product to be tested to a 100 ml bottle equipped with a rubber septum top stored for 3 months)

| Material | Aldehyde (Head Space analysis) | Odor |
| --- | --- | --- |
| Temperature 20° C. Compounds of the present invention | | |
| Example 1 | None Detected | Good |
| Example 2 | None Detected | Good |
| Example 3 | None Detected | Good |
| Unsaturated compound - not of the present invention | | |
| Oleyl Imidazoline | 120 ppm | Poor |
| Temperature 50° C. Compounds of the present invention | | |
| Example 1 | None Detected | Good |
| Example 2 | None Detected | Good |
| Example 3 | None Detected | Good |
| Unsaturated compound - not of the present invention | | |
| Oleyl Imidazoline | 220 ppm | Unacceptable |

I claim:

1. An imidazoline prepared by the reaction of aminoethylethanolamine which conforms to the following structure:

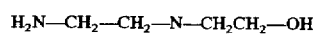

and
a meadowfoam compound selected from the group consisting of meadowfoam oil, meadowfoam methyl ester and meadowfoam acid.

2. A compound of claim 1 wherein said meadowfoam compound is meadowfoam oil.

3. A compound of claim 1 wherein said meadowfoam compound is meadowfoam fatty acid.

4. A compound of claim 1 wherein said meadowfoam compound is meadowfoam fatty methyl ester.

5. An imidazoline composition which comprises the following:

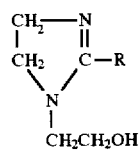

R is derived from meadowfoam and is:
60–65% by weight —$(CH_2)_3$—$CH=CH$—$(CH_2)_{13}$—$CH_3$
12–20% by weight a mixture of

—$(CH_2)_3$—$CH=CH$—$(CH_2)_{15}$—$CH_3$ and

—$(CH_2)_{11}$—$CH=CH$—$(CH_2)_7$—$CH_3$ and

15–28% by weight

—$(CH_2)_3$—$CH=CH$—$(CH_2)_6$—$CH=CH$—$(CH_2)_6$—$CH_3$.

\* \* \* \* \*